United States Patent
Kawasaki et al.

(10) Patent No.: US 7,164,481 B2
(45) Date of Patent: Jan. 16, 2007

(54) COEFFICIENT OF LINEAR EXPANSION MEASURING APPARATUS AND COEFFICIENT OF LINEAR EXPANSION MEASURING METHOD

(75) Inventors: Nobuo Kawasaki, Nerima-ku (JP); Toshihide Nakajima, Akishima (JP); Masahiko Daimon, Sagamihara (JP); Osamu Okajima, Sagamihara (JP)

(73) Assignee: Kabushiki Kaisha Ohara, Sagamihara (JP)

( * ) Notice: Subject to any disclaimer, the term of this patent is extended or adjusted under 35 U.S.C. 154(b) by 217 days.

(21) Appl. No.: 10/927,057

(22) Filed: Aug. 27, 2004

(65) Prior Publication Data

US 2005/0046869 A1 Mar. 3, 2005

Related U.S. Application Data

(60) Provisional application No. 60/499,920, filed on Sep. 4, 2003.

(30) Foreign Application Priority Data

Sep. 1, 2003 (JP) ............... 2003-308931

(51) Int. Cl.
*G01B 9/02* (2006.01)
*G01B 11/02* (2006.01)
*G01B 11/28* (2006.01)
*G01B 11/06* (2006.01)
*G01L 1/24* (2006.01)
*G02B 6/00* (2006.01)
*G02B 6/12* (2006.01)

(52) U.S. Cl. ............... 356/519; 385/12; 385/14; 385/134; 385/147; 356/35.5; 356/496; 356/503; 356/630; 356/632; 356/634

(58) Field of Classification Search ............... 356/35.5, 356/496, 503, 519, 630, 632, 634; 385/12, 385/14, 134
See application file for complete search history.

(56) References Cited

U.S. PATENT DOCUMENTS

| 3,619,463 | A | 11/1971 | Budin et al. |
| 3,930,730 | A | 1/1976 | Laurens et al. |
| 5,920,392 | A | 7/1999 | Tsai et al. |
| 6,466,308 | B1 * | 10/2002 | Jaing et al. ............... 356/35.5 |
| 2003/0103550 | A1 | 6/2003 | Davis et al. |

FOREIGN PATENT DOCUMENTS

| EP | 0 417 934 A2 | 3/1991 |
| JP | 06201620 A * | 7/1994 |
| JP | A 06-201620 | 7/1994 |
| JP | 11183413 A * | 7/1999 |
| JP | A 11-183413 | 7/1999 |

OTHER PUBLICATIONS

ASTM (American Society for Test and Materials); Designation: E289-99; "Standard Test Method for Linear Thermal Expansion of Rigid Solids with Interferometry"; pp. 1-9.

* cited by examiner

*Primary Examiner*—Frank G. Font
*Assistant Examiner*—Jerry Martin Blevins
(74) *Attorney, Agent, or Firm*—Oliff & Berridge, PLC

(57) ABSTRACT

A coefficient of linear expansion measuring apparatus includes: two reflection plates between which a sample is put, a container to house them, which is filled with a gas having known rate of a refractive index variation, a temperature regulating member to set a temperature in the container variably, a light source to irradiate an irradiating light to reflecting surfaces of the reflection plates, a light receiving element to receive reflected lights in which the lights interferes each other and detecting a light intensity thereof, and a calculating member to calculate a coefficient of linear expansion of the sample, wherein: the calculating member calculates an optical path length variation between the reflecting surfaces from an output variation of the light receiving element, and calculates a length variation of the sample by correcting a part of the optical path length variation derived from the refractive index variation of the gas caused by the temperature variation.

20 Claims, 5 Drawing Sheets

COEFFICIENT OF LINEAR EXPANSION MEASURING APPARATUS AND COEFFICIENT OF LINEAR EXPANSION MEASURING METHOD

This application is entitled to the benefit of Provisional Patent Application No. 60/499,920, filed on Sep. 4, 2003.

BACKGROUND OF THE INVENTION

1. Field of the Invention

The present invention is related to a coefficient of linear expansion measuring apparatus and coefficient of linear expansion measuring method where a coefficient of linear expansion of a sample is measured from an optical path length variation of reflected lights reflected on two reflection plates having a sample between them.

2. Description of Related Art

As for an apparatus for measuring a coefficient of linear expansion of a sample, what is called Fizeau interferometer and Michelson interferometer of double optical paths type can be given, where a sample is put between two reflector plates in the condition of tilting reflecting surfaces thereof each other slightly, a light having a known wavelength is irradiated from a single light source to each reflecting surface under vacuum, and an amount of expansion according to a temperature variation is measured by shift of interference fringes variation arisen by a interference of reflected lights (for example, see JIS R3251, appendix, 1995).

Many of the coefficient of linear expansion measuring techniques in earlier development have a constitution where shift of interference fringes and the variation thereof are observed and measured visually. Thus, it has been problematic that a user is under a large burden, and the possible deviation of test results depending on a user results less reproducibility.

In order to reduce a burden to a user, a measuring apparatus designed for automation is available in the market (ULVAC-RIKO, Inc.). However, imaging by an imaging member and image processing such as digitalization of the imaged data and the like are required for measuring and digitalizing shift of interference fringes variation. Thus, there have been problems such as complication of the equipment, decrease of the productivity and increase of the production cost thereof.

SUMMERY OF THE INVENTION

The object of the invention is to reduce a burden to a user in measuring a coefficient of linear expansion of a sample, and another object is to simplify the measuring equipment.

According to the first aspect of the invention, a coefficient of linear expansion measuring apparatus comprising: two reflection plates between which a sample is put, a container to house the sample and the reflection plates, the container being filled with a gas having known rate of a refractive index variation, a temperature regulating member to set a temperature inside the container variably, a single light source to irradiate an irradiating light having a known wavelength to reflecting surfaces of the reflection plates placed in the container, a light receiving element to receive an reflected lights reflected on the reflection plates in a condition that the reflected lights interferes each other and to detect a light intensity of the reflected lights, and a calculating member to calculate a coefficient of linear expansion of the sample, wherein the calculating member calculates an optical path length variation between the reflecting surfaces of the individual reflection plates from an output variation of the light receiving element according to temperature variation in the container, and the calculating member calculates a length variation of the sample by correcting a part of the optical path length variation derived from a refractive index variation of the gas in the container caused by the temperature variation.

In the above constitution, the reflection plates are installed in the container, where the reflecting surfaces thereof are parallel each other and a sample is put between the reflection plates. Here, the reflection plates are installed where the reflecting surface side thereof are faced each other and the sample is located between them. That is, the clearance between the reflecting surfaces corresponds to the width of the sample.

Light having a known wavelength is irradiated perpendicularly from an opposite side of the reflecting surface side of either reflection plate. A part of the light having a known wavelength is half reflected on the reflecting surface of the former reflection plate, and the other part of the light transmitting through the former reflection plate is reflected on the reflecting surface of the latter reflection plate.

Accordingly, the difference of path between the former reflected light and latter reflected light is twice as long as a width of the sample. The reflected lights enter the light receiving element with interfering each other, and the light intensity thereof is detected.

The gas having known rate of refractive index variation fills the container, and a temperature variation is given to the sample in this condition. It is to be noted that the rate of refractive index variation of the gas designate a variation according to a temperature, However, when an internal pressure of the container varies, a gas is used where the rate of the refractive index variation thereof according to a pressure is also known. That is, the rate of the refractive index variation of the gas includes a variation according to a given temperature variation and a variation according to a pressure variation in a course of the measurement. However, the pressure variation is not taken into account in real-time in the measurement, and in the present invention, assumed situation are such that the container has a structure which does not generate a pressure variation, the calculating member memorizes a general or steady pressure value, and a numeral value of a pressure is input and the refractive index is compensated according to the input value. However, a pressure variation of the gas may be taken into account in the invention.

Accordingly, the output variation of the light receiving element according to the given temperature variation represents the sum of the refractive index variation of the gas in the container and the variation according to the expansion of the sample.

The calculating member calculates a phase contrast from a light intensity variation according to the temperature variation and further calculates an optical path length variation between the reflection plates from the phase contrast, the known wavelength of the irradiation light and the known refractive index of the gas. It is to be noted here that the calculated optical path length variation is affected by the refractive index variation of the gas in the container. Thus, it does not represent the geometric length variation of the sample caused by the expansion thereof. For this reason, a refractive index variation in the range of temperature varied is calculated and a part of the optical path length variation derived from the calculated refractive index variation is deducted from the optical path length variation previously calculated from the detected light intensity variation, so that a length variation of the sample is calculated.

Finally, it becomes possible that the coefficient of linear expansion of the sample is calculated from the length variation of the sample and the temperature variation.

When the part of the optical path length variation derived from the refractive index variation of the gas in the container is corrected, the calculating member may calculate the length variation of the sample in each interval of peaks which are maximum or minimum in a continuous wave pattern of a light intensity variation output from the light receiving element, and simultaneously refers a refractive index of the gas at temperatures at each of the peaks.

In correcting a part of the optical path length variation derived from the refractive index variation, the expansion and contraction length of the sample is calculated in each interval of peaks which are maximum or minimum in a continuous wave pattern of the light intensity variation output from the light receiving element. That is, the expansion and contraction length of the sample is calculated in each interval that is from a high peak to an adjacent low peak, or from a low peak to an adjacent high peak in a continuous wave pattern of the light intensity.

Temperatures at peaks or bottoms on both sides of the interval are measured and the refractive indexes at the temperatures are calculated.

When a certain temperature at which the light intensity shows a maximum or minimum point is set as a standard temperature, the length variation of the sample from the length at a standard temperature can be represented by functions of the number of cycles of the light intensity variation from the standard temperature, a known wavelength of the irradiating light under vacuum, a sample length at the standard temperature, a refractive index of the gas at the standard temperature, a refractive index of the gas at each maximum or minimum point in the light intensity variation (see formula (8), (12), (13) and the like described below). A measured cyclic variation of the detected light intensity according to a temperature variation, i.e. the frequency thereof, is remarkably high in a gas filled in the container compared to under vacuum. For this reason, obtaining the length variation at maximum or minimum point makes it possible to calculate a microscopic variation at each temperature.

The sample may have a midair through-hole to pass the irradiating light having the known wavelength therethrough is provided with the sample.

In the above constitution, since the sample has a midair through-hole, an irradiation point of the irradiating light dose not have to be at a corner being away from a sample. Further, since the irradiating light passes though the through-hole where gas flow hardly occurs, an effect of gas fluctuation is prevented. Thus, the light intensity is detected stably.

Further, since the optical path which is to be the optical path difference goes inside the sample, a temperature difference between the sample and the optical path is reduced.

The coefficient of linear expansion measuring apparatus preferably comprise a pressure detecting member to detect a pressure variation of the gas in the container, wherein the calculating member calculates the refractive index of the gas from a temperature and a detected pressure in the container.

The above constitution is successful in producing same effect of the invention, wherein the pressure variation in the container is further detected and the calculating member calculates the refractive index further on the ground of the detected gas pressure so as to calculate the length variation of the sample by correcting a part of the optical path length variation derived from the refractive index variation of the gas in the container.

According to the second aspect of the invention, a coefficient of linear expansion measuring method comprising: housing two reflection plates and a sample to a container being capable of controlling a temperature, where a sample is put between the reflection plates and reflecting surfaces of reflection plates are parallel with each other, filling the container with a gas having a known refractive index variation before as well as after the housing, irradiating an irradiating light having a known wavelength to the reflecting surfaces of the reflection plates placed in the container by a single light source, detecting a light intensity of reflected lights reflected on the reflection plates in a condition that the reflected lights interfere each other, while a temperature variation is given to the sample placed in the container, calculating an optical path length variation between the reflecting surfaces of the reflection plates from an output variation of the light receiving element according to the temperature variation, correcting a part of the optical path length variation derived from a refractive index variation of the gas in the container caused by the temperature variation, and calculating a length variation of the sample.

In the above constitution, a reflected light reflected on the reflection surface of the one reflection plate interferes with that reflected on the reflection surface of the other reflection plate placed in the container, where a optical path difference between them is twice as long as the width of the sample, and the light intensity thereof is detected by the light receiving element.

The temperature variation is given in the condition where the container is filled with the gas having known rate of a refractive index variation. That is, the refractive index variation of the gas includes a variation according to a given temperature variation and a variation according to a pressure variation in a course of the measurement. However, in the present invention, assumed situations are such that the container has a structure which does not generate an internal pressure variation, the calculating member has a memory of a general or steady pressure value, and a numeral value of a pressure is input and the refractive index is calculated according to the input value. However, a pressure variation of the gas may be taken into account in the invention.

Accordingly, the output variation of the light receiving element according to a given temperature variation represents the sum of the variation according to refractive index variation of the gas in the container and the variation according to the expansion of the sample.

Accordingly, the phase variation is observed in the condition where the refractive index of the gas in the container affects it.

When the length variation of the sample is measured, not only the optical path difference between the reflecting surfaces is measured from the phase difference of the detected light intensity, but also a part of the optical path length variation derived from the refractive index of the gas in the container is obtained. The geometrical length variation of the sample in the container is calculated from the difference between the above two.

Finally, it becomes possible that the coefficient of linear expansion of the sample is calculated from the length variation of the sample and the temperature variation.

When the part of the optical path length variation derived from the refractive index variation of the gas in the container is corrected, the length variation of the sample may be calculated in each interval of peaks which are maximum or minimum in a continuous wave pattern of a light intensity variation output from the light receiving element, and simultaneously a refractive index of the gas at temperatures at the individual peaks is referred.

In correcting a part of the optical path length variation derived from the refractive index variation, the length variation of the sample is calculated in each interval of peaks which are maximum or minimum in a continuous wave pattern of the light intensity variation output from the light receiving element. That is, the expansion and contraction amount of the sample is calculated in every interval of from a high peak to an adjacent low peak or from a low peak to an adjacent high peak.

The temperatures at peaks on every side of the interval are measured and the refractive indexes at the temperatures are calculated.

When a certain temperature at which the light intensity shows a maximum or minimum point is set as a standard temperature, the length variation of the sample from the length at a standard temperature can be represented by functions of the number of cycles of the light intensity variation from the standard temperature, a known wavelength of the irradiating light under vacuum, a sample length at the standard temperature, a refractive index at the standard temperature, a refractive index at each maximum or minimum point in the light intensity variation (see formulas (8), (12), (13) and the like described below). A cyclic variation of the detected light intensity according to a temperature variation, i.e. the frequency thereof, is remarkably high in a gas filled in the container comparing to that under vacuum. For this reason, measuring the length variation at maximum or minimum point makes it possible to calculate a microscopic variation at each temperature.

A midair through-hole may be provided with the sample and a measurement is performed in which the irradiating light having the known wavelength transmits one reflection plate, passes through the midair through-hole and is irradiated to other reflection plate.

In the above constitution, since the sample has a midair through-hole, an irradiation point of the irradiating light dose not have to be at a corner being away from a sample. Further, since the irradiating light passes the through-hole where gas flow hardly occurs, an effect of gas fluctuation is prevented. Thus, the light intensity is detected stably.

Further, since the optical path which is to be the optical path difference goes inside the sample, a temperature difference between the sample and the optical path is reduced.

The coefficient of linear expansion measuring method preferably comprises: detecting a pressure variation of the gas in the container, and calculating the refractive index of the gas from a temperature and a detected pressure in the container.

In the above constitution, the pressure variation in the container is further detected and the refractive index is further calculated on the ground of the detected gas pressure so that the length variation of the sample is calculated by correcting a part of the optical path length variation derived from the refractive index variation of the gas in the container.

Since the invention has a constitution in which the light receiving element detects the light intensity variation of the irradiating light having a known wavelength according to an expansion of the sample, the output of the light receiving element can be coded and an expansion variation of a sample can be calculated by electrical processing. Accordingly, it becomes possible to reduce a burden to a user that a measurement is performed by visual observation in earlier development. Further, it becomes possible to exclude an effect of a difference between individual user's skills compared to an operation performed visually, and to perform a measurement having high reproducibility.

According to the first and second aspect of the invention, a measurement is performed by detecting a light intensity variation. Thus, an imaging member is not used unlike in the case of observing shift of interference fringes in earlier development, a measurement result can be recorded and further can be processed, and furthermore, an image processing apparatus is not required. As a result, it becomes possible to simplify the equipment and to reduce the cost for the equipment.

According to the first and second aspect of the invention, the measurement is performed in which a sample is put under an atmosphere of a gas having a known rate of refractive index variation. Thus, in measuring a coefficient of linear expansion of a sample, when the effect to the detected light intensity variation according to the expansion variation of the sample is lower than that according to a refractive index of a gas, the detected wave pattern of the light intensity has higher cycle than that obtained by a measurement performed under vacuum in the same range of temperature variation. In a measurement performed under vacuum, when the temperature range is narrow, a length variation of a sample is measured from a slight phase shift less than a half of a cycle in a light intensity variation curve, and it is required for specifying the amount of phase shift that a maximum value and a minimum value are detected. Further in earlier development, since the temperature variation between a maximum point and minimum point (or a minimum point and a maximum point) is wide, the measurement is vulnerable to modulation of the light source and light receiving element in the long-period variation. Thus, decrease of accuracy due to them has been problematic. On the other hand, the present invention is successful in obtaining detected wave pattern having high frequency of the light intensity variation. Thus, a phase shift variation is easily recognized, error of recognition is prevented, and it becomes possible to perform a measurement having high reliability even in a measurement performed in a narrow range of temperature. Further, as long as a refractive index of a gas at each temperature is obtained accurately, the effect thereof can be accurately excluded. Thus, it is possible to obtain a coefficient of linear expansion of a sample with higher accuracy compared with that in earlier development.

Since the temperature variation is given to a sample in an atmosphere of a gas, conduction of heat is fast thanks to gas convection. Thus, it becomes possible to perform a rapid measurement since a waiting period for normalizing a temperature difference between a sample and optical path is decreased.

Since the temperature variation is given to a sample in an atmosphere of a gas, positions of maximum and minimum points in the continuous wave pattern become clear. Thus, error of recognition of phase shift variation due to the modulation of the light source and the noise of the light receiving element is reduced and it becomes possible further to reduce error of recognition and to improve reliability.

Further the apparatus does not require equipment having high quality such as a light source showing no modulation and a light receiving element generating no noise, and equipment having high accuracy such as a light receiving element being capable of detecting micro variation. Thus it becomes possible to simplify the equipment and to reduce the cost of equipment.

According to the invention, the length variation of the sample is measured in each interval of peaks recognized clearly in the continuous wave pattern. Further, the refractive index is calculated in every peak points which are maximum points or minimum points. Thus it becomes possible that the error of the recognition is further prevented and the reliability is further improved. Furthermore, compared to a measurement performed under vacuum, length variation of a sample is measured in every maximum point and minimum point in the continuous wave pattern having higher frequency. Thus, it becomes possible to reduce error of recognition of phase shift variation due to the modulation of the light source and the noise of the light receiving element and amplifiers thereof. As a result, it becomes possible that the error of the recognition is further prevented and the reliability is further improved.

Further the apparatus does not require equipment having high quality such as a light source showing no modulation and a light receiving element generating no noise, and equipment having high accuracy such as a light receiving element being capable of detecting micro variation. Thus it becomes possible further to simplify the equipment and to reduce the cost for the equipment.

According to the invention, a midair through-hole is provided with a sample, an irradiation spot of the irradiating light dose not have to be at a corner for being away from a sample. Further, since the irradiating light passes through the through-hole where gas flow hardly occurs, an effect of gas fluctuation is prevented. Accordingly, the light intensity is detected stably and error in calculating the length variation of the sample can be effectively prevented. Further, since the optical path which is to be the optical path difference goes inside the sample, the temperature difference between the sample and the optical path is reduced. Thus, temperature differences in the parts are reduced and it becomes possible to perform a measurement having high reliability and high precision.

According to the invention, the pressure variation of the gas in the container is detected in the measurement. Since the measured pressure is taken into account in calculating the refractive index of the gas, it is possible to calculate the refractive index even in an environment where the pressure of the gas varies. Thus, it becomes possible to measure the length variation of the sample more precisely.

BRIEF DESCRIPTION OF THE DRAWINGS

The present invention will become more fully understood from the detailed description given hereinbelow and the appended drawings which given by way of illustration only, and thus are not intended as a definition of the limits of the present invention, and wherein.

DETAILED DESCRIPTION OF THE PREFERRED EMBODIMENTS

Hereinafter, a feature of the present invention will be explained in detail as an embodiment.

(Whole Constitution of the Embodiment)

Figure 1:
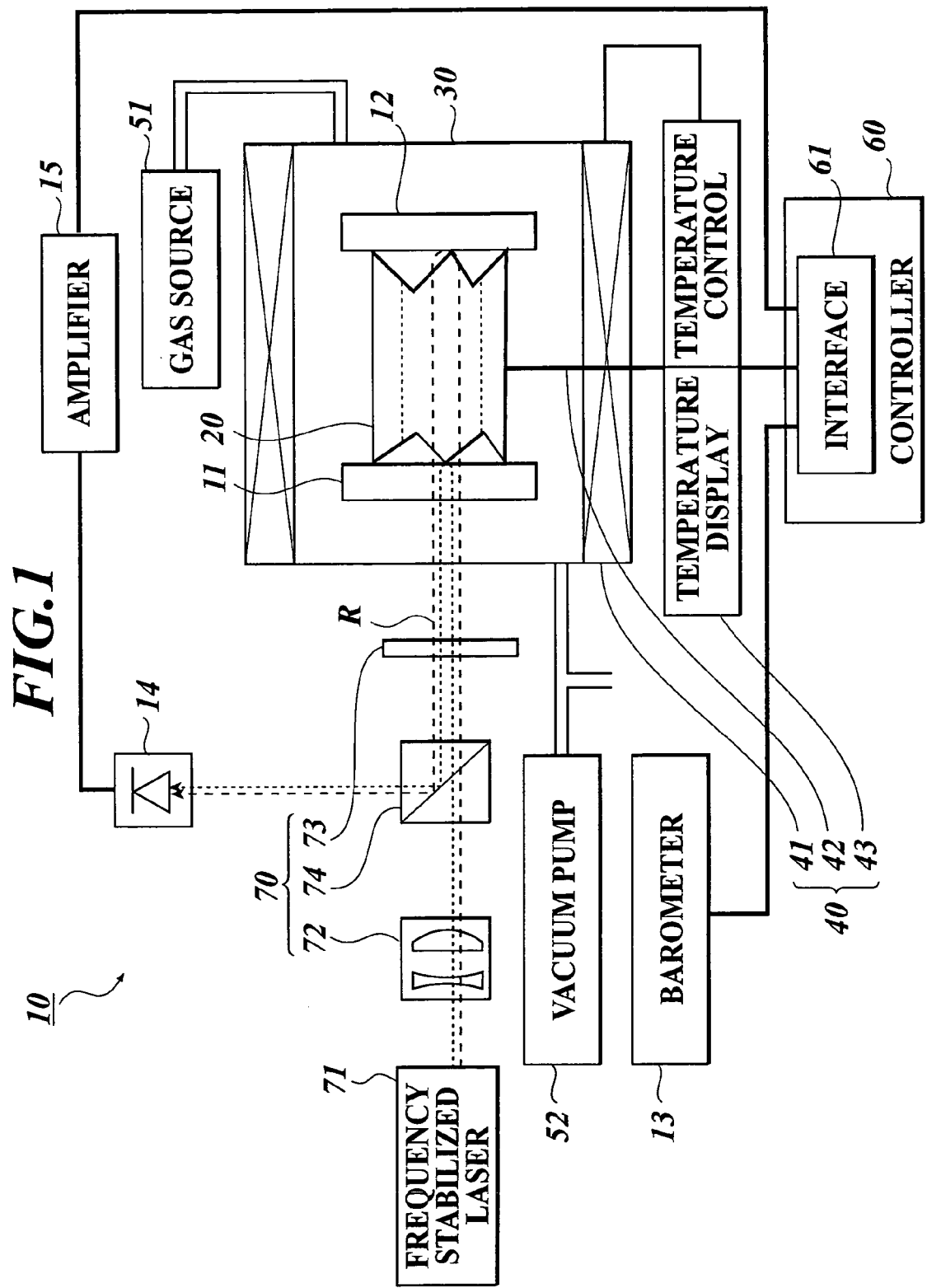
FIG. 1 is a block diagram showing the schematic constitution of the coefficient of linear expansion measuring apparatus.

A coefficient of linear expansion measuring apparatus 10, which is the embodiment of the present invention, will be described with reference to FIG. 1 to FIG. 5. FIG. 1 is a block diagram showing a schematic constitution of the coefficient of linear expansion measuring apparatus 10.

The coefficient of linear expansion measuring apparatus 10 comprises: a couple of reflection plates 11 and 12 where a sample 20 is put between the reflection plates, a container 30 for housing the sample 20 and the reflection plates 11 and 12, the container being filled with a gas having known rate of refractive index variation, a temperature regulating member 40 to regulate a temperature of the sample 20 in the container 30, an internal gas supplying member to supply the gas having known rate of refractive index variation to the container 30, frequency stabilized laser 71 as a single light source to irradiate a laser R having a known wavelength to reflecting surfaces 11a and 12a of the individual reflection plates 11 and 12, an optical system 70 of the laser 71, a light receiving element 14 to receive an reflected lights of the individual reflection plates 11 and 12 with the light interfering each other so as to detect a light intensity thereof, an barometer 13 as a pressure detecting member to detect a pressure corresponding to the pressure in the container 30 and a controller 60 as a calculating member to calculate a coefficient of linear expansion of the sample 20 in the container 30.

Hereinafter, each member will be described in detail.

(Sample)

Figure 2:
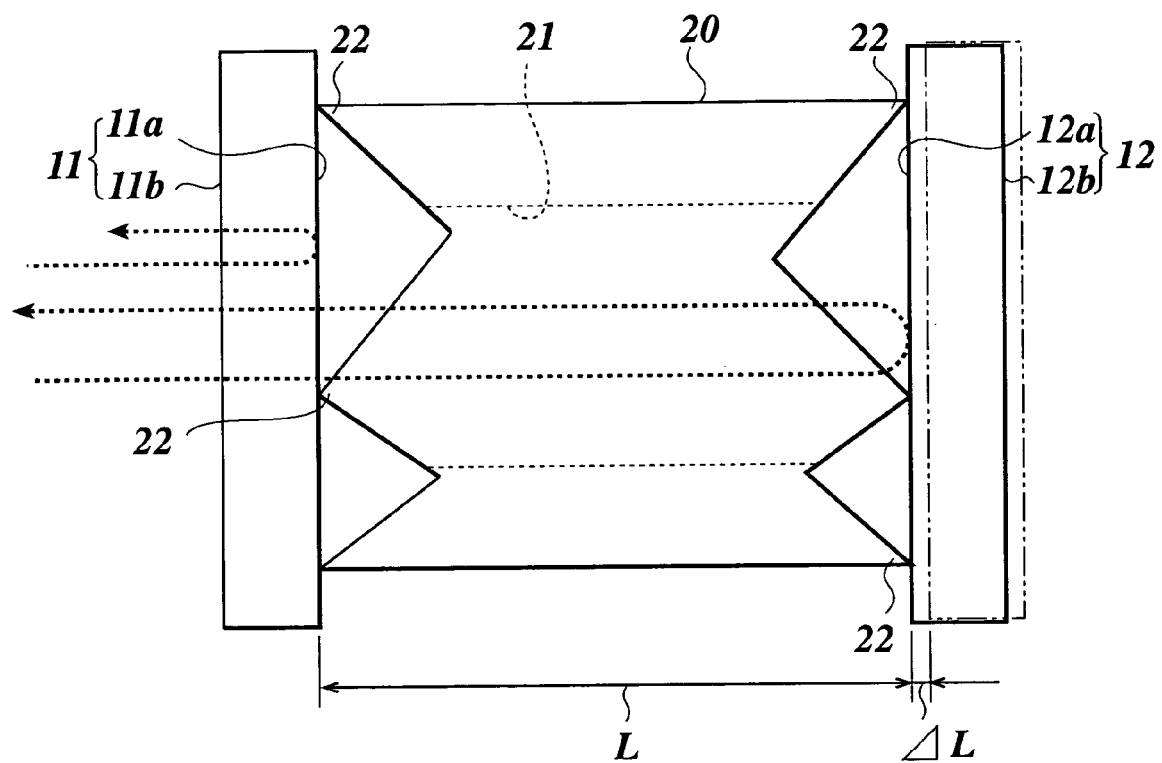
FIG. 2 is an explanatory drawing showing the condition of the sample and two reflection plates placed in the container.

FIG. 2 is a view to explain a condition of the sample 20 and reflection plates 11 and 12 which are installed in the container 30.

The sample 20 is a block-like object consisting of a material, the coefficient of linear expansion of which is to be measured. The material is not limited, but in particular, a material having low coefficient of linear expansion such as a low expansion glass is suitable. A through-hole 21 is formed at the center part of the sample 20. The through-hole 21 is formed to transmit a laser light of the frequency stabilized laser 71. The reflection plates 11 and 12 are respectively provided at each end in the direction of the center line of the through-hole 21 in which the plates are contacted with the sample 20. Three convex parts 22 are formed respectively on the each end part of the sample 20, which contact with the reflection plates 11 and 12 respectively. The three convex parts 22 are formed, where tips thereof on the each end part of the sample 20 are respectively located on the same plane, and the plane defined by the three convex parts 22 on the one end part is parallel to the plane defined by that on the other end part.

(Reflection Plate)

The two reflection plates 11 and 12 are disks made up of zero expansion glass in the container 30, and one reflection plate 11 is placed on one side of the sample 20 from which the laser light R enters, and the other reflection plate 12 is placed on the opposite side of the sample 20. Here, the sample 20 is put between the reflection plates 11 and 12. Hereinafter, let the one reflection plate represent a first reflection plate 11 and let the other reflection plate represent a second reflection plate 12.

Both sides of the first reflection plate 11 are optical-polished planes. It is desirable that the flatness thereof is ¼ or less of the wavelength of the laser light R. One plane of the first reflection plate 11 works as a reflecting surface 11a of the laser light R, and the reflecting surface 11a is placed to contact with the sample 20. The other plane 11b slightly inclines to the reflecting surface 11a (for example 1°, the angle of gradient is not limited). The laser light R is set to enter perpendicularly the reflecting surface 11a thanks to the after-mentioned optical system 70. When the laser light R enters, both the reflecting surface 11a and the plane 11b reflect a part of the laser light R. However, since the reflection direction thereof are different each other, and the light receiving element 14 is set to receive only the reflected light of the reflecting surface 11a.

Either side of the second reflection plate 12 is an optical-polished plane which works as a reflecting surface 12a. It is desirable that the flatness thereof is less than ¼ of the wavelength of the laser light R. The other side thereof is a plane of a frosted glass, so as to diffuse a laser light.

The second reflection plate 12 is placed in the container 30, in which the reflecting surface 12a is contacted with the sample 20 and is perpendicular to the laser light R. The reflection plate 12 reflects the laser light R which has transmitted the first reflection plate 11 and passed the through-hole 21 of the sample 20. The reflected light reflected on the reflecting surface 11a of the first reflection plate 11 and the reflected light reflected on the reflecting surface 12a of the second reflection plane 12 goes along a same line in an inverse direction to the entered direction with the lights interfering each other, in which the optical path difference of them is twice as long as the width of the sample 20 (the distance between the reflecting surfaces 11a and 12a).

(Frequency Stabilized Laser and the Optical System Thereof)

As for the frequency stabilized laser 71, a laser emitting a single wavelength light of known wavelength is used, and He-Ne laser is one of examples. However, a type of the laser is not limited.

The frequency stabilized laser 71 is placed so as to emit the laser light R in a direction perpendicular to the reflecting surfaces 11a and 12a of the reflection plates 11 and 12 placed in the container 30.

The optical system 70 comprises a beam expander 72 to regulate the beam diameter of the laser light R emitted from the frequency stabilized laser 71, a quarter-wave plate 73 placed between the beam expander 72 and the container 30 and a beam splitter 74 placed between the beam expander 72 and the quarter-wave plate 73 to transmit the emitted light from the frequency stabilized laser 71 and to reflect the reflected light from the reflection plates 11 and 12 perpendicularly.

The laser light R emitted from the frequency stabilized laser 71 transmits the beam splitter 74, is reflected on the reflecting surfaces 11a and 12a of the reflection plate 11 and 12 and is back to the beam splitter 74. When the laser light R is back to the beam splitter 74, it has passed through the quarter-wave plate twice and the direction of polarization thereof is rotated to the perpendicular direction. Thus, the reflected light does not pass through straightly but is reflected perpendicularly on the beam splitter 74.

(Light Receiving Element)

The light receiving element 14 is placed at the destination to which reflected laser light R reflected by the beam splitter 74 goes, and receives the reflected light reflected on the reflection plates 11 and 12 so as to outputs a signal according to the light intensity thereof. As for the type of the light receiving element, any light receiving elements being capable of outputting an electric signal in accordance with light intensity of a received light, and a silicon photodiode is used as one of examples.

The output signal of the light receiving element 14 is output via the amplifier 15 to the controller 60.

(The Container and Internal Gas Supplying Member)

The container 30 is a cover body being capable of housing the sample 20 and the reflection plates 11 and 12, and has a heat insulated structure against outside. The internal gas supplying member to supply dry air containing a constant content of carbon dioxide as the gas having known rate of refractive index variation is arranged in the container 30. The internal gas supplying member comprises a gas source 51 to generate a dry air in which the moisture thereof has been removed by silica gel and a vacuum pump 52 to discharge gas in the container 30. That is, when the pressure inside the container 30 is decreased by the vacuum pump 52, the gas source 51 supplies the dry air. Small amount of gas is continuously flown and also discharged for preventing external atmosphere from penetrating into the container 30 directly. Accordingly, the supply and discharge of dry air keeps the pressure inside the container 30 almost as same as atmospheric pressure.

As for the supplied gas, any gas can be give as long as its rate of refractive index variation according to a composition, temperature, pressure, humidity and the like can be calculated. For example, inert gas and the like where nitrogen, argon, helium, carbon dioxide and the like are main component may be used.

(Barometer and Temperature Regulating Member)

The barometer 13 detects atmospheric pressure in a course of the measuring and outputs it to the controller 60. As described above, the pressure in the container 30 is kept corresponding to atmospheric pressure. Atmospheric pressure is detected in order to refer to it as the pressure of dry air in the container 30.

The temperature regulating member 40 comprises a heating and cooling member 41 to regulate the temperature in the container 30, a temperature detector 42 to measure the temperature of the sample 20 and a temperature controller 43 to perform heating and cooling controls according to the heating and cooling member 41.

As for the heating and cooling member 41, any device which can heat and cool the atmospheric temperature in the container 30 can be given. For example, a heat exchanger, Peltier element and the like can be used.

The temperature detector 42 is a thermocouple which is inserted into an insert hole provided to the sample 20.

The temperature controller 43 controls heating and cooling condition of the heating and cooling member 41 according to the detected temperature of the temperature detector 42, so as to regulate the temperature of the sample 20 to the target temperature set by the controller 60. A monitor to display the current temperature of the sample is provided with the temperature controller 43.

(Controller)

The controller 60 comprises a ROM to which a processing program and processing data to execute the after-mentioned processes performed by the coefficient of linear expansion measuring apparatus 10 is written, a CPU to execute the above processes according to the processing program and a RAM to memorize the various processing data of the CPU.

The RAM comprises various working memories, counters and the like, and is also used as a working area in the processes.

The controller 60 is connected to the barometer 13, the amplifier 15 of the light receiving element 14 and the temperature controller 43 via an interface 61, and receiving output data thereof to sample the variation of atmosphere pressure, receiving light intensity and sample temperature as data.

Concretely, the controller 60 performs the following processes.

(1) In changing the temperature in the container 30 from an initial temperature to a target temperature by the temperature controller 43, the controller 60 performs a process to calculate a phase difference caused by the temperature variation from the continuous wave pattern of an light intensity variation based on the output of the light receiving element 14. Further, the controller 60 performs a process to calculate an optical path length variation from the phase difference and a known wavelength of the laser light.

(2) The controller 60 performs a process to calculate the length variation of the sample 20 by correcting a part of the optical path length variation derived from a refractive index variation due to the temperature variation and atmospheric pressure variation of dry air in the container 30.

(3) The controller 60 performs a process to calculate the coefficient of linear expansion of the sample 20 from the obtained length variation of the sample 20.

The above-described process (1) will be further described in detail. The path difference of the laser light R is generated according to the distance between the reflecting surfaces 11a and 12a of the reflection plates 11 and 12 (the path difference corresponds to twice as long as the width of the sample 20).

The light receiving element 14 receives the reflected lights reflected on the reflecting surfaces 11a and 12a interfering with each other, so as to detects the light intensity of the interfering light which interferes each other according to the optical path difference.

That is, the laser light reflects on the first reflection plate 11 where no phase shift is given in the reflection. On the other hand, the laser light transmitting the first reflection plate 11 reflects on the second reflection plate 12 where a phase difference of half wavelength ($\pi$) is given in the reflection and a phase difference according to the optical path difference represented as product of the path difference and a refractive index of dry air is also given.

When a temperature variation is given, the optical path difference varies according to the length variation of the sample 20 due to the thermal expansion thereof and the refractive index variation of the dry air. Thus, the phase difference between the reflected lights interfering each other varies. Therefore, the light intensity variation shows a continuous wave pattern when the detected light intensity is sampled corresponding to the predetermined temperature variation (see S1 in FIG. 3).

The controller 60 calculates the phase variation from the sampled light intensity variation. The variation of the optical path length is obtained from the obtained phase variation and the wavelength of the laser light.

The above-described process (2) is further described in detail. The optical path length variation calculated by the process (1) dose not correspond to the distance twice as long as the length variation of the sample 20, since the optical path length variation is affected by the refractive index of the dry air in the container 30. Therefore, a part of the optical path length variation derived from the refractive index variation of the dry air in the container 30 is calculated and is subtracted from the optical path length variation in (1).

Figure 3:
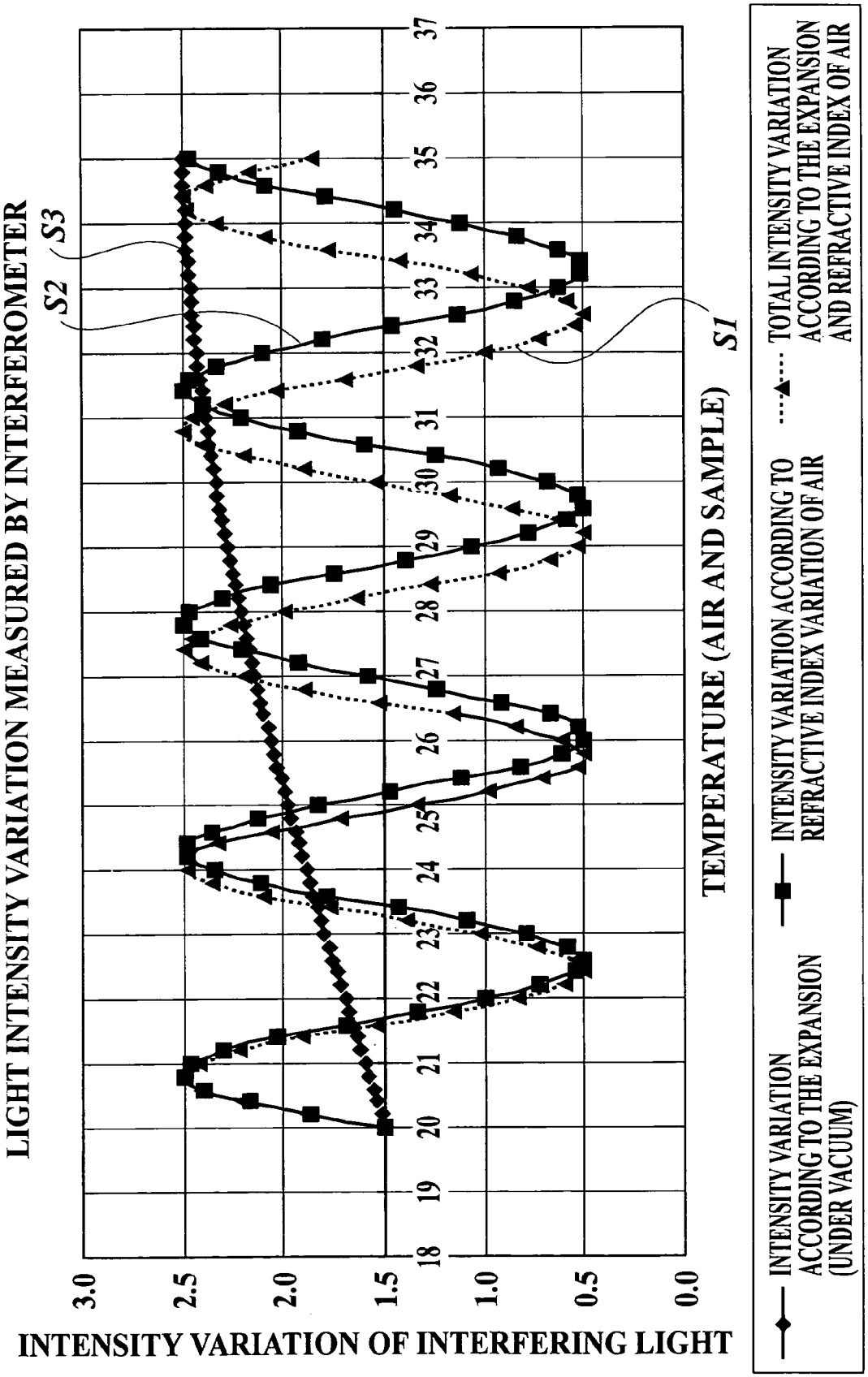
FIG. 3 is a simulated diagram showing the relation between the temperature variation and the light intensity variation due to the temperature variation.

FIG. 3 is a simulated diagram showing a relation of the temperature variation and the light intensity variation of low thermal expansion material caused by the temperature variation. S1 designates the detected light intensity variation based on the optical path length variation due to the width variation (length variation) of the sample 20 including the effect of the refractive index variation of the dry air. S2 designates the detected light intensity variation based on the optical path length variation only due to the effect of refractive index of the dry air, obtained in the condition where the sample 20 is absent (i.e. the condition where actual distance between the reflection plates 11 and 12 does not varies). S3 designates the detected light intensity variation based on the optical path length variation only due to the width variation of the sample 20, obtained under vacuum.

Depending on the relation between a coefficient of linear expansion of the sample and a wavelength of the laser light, when there is no effect of the dry air, the cycle of the plotted continuous wave pattern is large in the present embodiment, which is shown as S3 in FIG. 3 (only about $\lambda/4$ of the wave pattern is drawn in FIG. 3.), since the length variation of the sample 20 based on the temperature difference is minute. On the other hand, the effect of the refractive index variation of the dry air based on the temperature variation is large, and the wave pattern shown as S2 includes a plurality of cycles. Therefore, it is required that the effect of the refractive index of the dry air is corrected.

Here, a refractive index variation of a dry air is explained.

When a certain gas is used as a medium in an optical path, the optical path length between certain two points $OPL_0$ is represented by the formula $OPL_0 = n_{gas} \cdot L_0$, where $L_0$ represents a geometrical distance between the two points and $n_{gas}$ represents the refractive index of the gas.

The refractive index of the gas $n_{gas}$ is determined by (1) gas kind and (2) gas density. Since the gas density can be regarded as the function of a gas temperature and gas pressure based on an equation of state of gas, it can be also said that the refractive index of the gas $n_{gas}$ is determined by (1) gas kind, (2) gas temperature T and (3) gas pressure P. That is, the refractive index of the gas can be represented as $n_{gas} = f_{gas}(T, P)$.

When the gas is air, which is a mixture of $N_2$, $O_2$, $CO_2$ and water vapor, the concentration variations of $N_2$ and $O_2$ in the gas are minute and negligible. Thus, the refractive index of air $n_{air}$ can be represented as $n_{air} = f_{air}(T, P, P_{vaper}$ and $CO_2$ concentration) by the Edlen's formula in which the refractive index of air is experimentally represents by functions of temperature T, pressure P, $CO_2$ concentration and water vapor pressure in the air $P_{vapor}$.

In the coefficient of linear expansion measuring apparatus 10, dry air in which the moisture thereof is removed by a silica gel is used to reduce an effect of a water vapor pressure. Further, the $CO_2$ concentration is regarded as being constant, and the variation thereof is not taken into account since the $CO_2$ concentration hardly varies in the measurement. Accordingly, the controller 60 detects the temperature variation of the gas by the thermocouple 42 and the gas pressure by the barometer 13 since the pressure in the container 30 is as high as atmospheric pressure, so that the refractive index of the dry air is calculated from them.

Next, a calculation method of the length variation of the sample performed by the controller 60, where an elimination of the effect of the refractive index of the dry air is taken into account, will be explained.

When the expansion of the sample 20 is measured in the dry air, the intensity of the interfering light varies faster (in higher frequency) compared with that under vacuum, so that several peaks of maximum and minimum shown as S1 in FIG. 3 occurs according to the measurement range. It is to be noted that the numerical value of the longitudinal axis in FIG. 3 represents the variation from a certain light intensity in the measurement.

Now, the conditions of destructive interference of light (minimum point) and constructive interference of light (maximum point) are considered. In the light of the fact that a phase shift of a half wavelength is given on the second reflecting surface 12a, the following formulas have equality in the above conditions. In the condition of destructive interference of light each other, $$2L = m\lambda \tag{1}$$

(where m cycles of wave of the light are included while the light goes to and from the sample length.)

In the condition of constructive interference of light, $$2L = \left(m + \frac{1}{2}\right)\lambda \tag{2}$$

(where m+½ cycles of wave of the light are included while the light goes to and from the sample length.)

wherein L represents the sample length at the condition, $\lambda$ represents the wavelength at the condition and m represents the order of interference (an integer, for example, which represents the number of waves included while the light goes to and from the sample length at the standard temperature at which the measurement starts).

(The Length Variation at a Minimum Point)

First, the formula representing the length variation in the condition of the destructive interference of light is considered and the condition is set as a standard. Let the order of interference at a certain minimum point represent m and let various values in the point represent as described below.

$L_m$: the sample length (at the point)
$t_m$: the temperature (at the point)
$\lambda_m$: the wavelength (at the point)
$n_m$: the gas refractive index (at the point)

The above are considered also at the other minimum points. Since the formula (1) has equality in a minimum point, the following formulas have equality.

$$2L_m = m\lambda_m \rightarrow \tag{3}$$

$$L_m = \frac{m}{2}\lambda_m \tag{3)'}$$

$$2L_{m+1} = (m+1)\lambda_{m+1} \rightarrow \tag{4}$$

$$L_{m+1} = \frac{m+1}{2}\lambda_{m+1} \tag{4)'}$$

$$\vdots$$

$$2L_{m+m'} = (m+m')\lambda_{m+m'} \rightarrow \tag{5}$$

$$L_{m+m'} = \frac{m+m'}{2}\lambda_{m+m'} \tag{5)'}$$

Thus, when the sample length $L_m$, where the order of interference is m, is set as a standard, the difference of length (length variation) between the standard and the length at each minimum points $L_{m+1}, L_{m+2} \ldots L_{m+m'}$, is represented by the following formulas.

$$\Delta L_1 = L_{m+1} - L_m = \frac{m+1}{2}\lambda_{m+1} - \frac{m}{2}\lambda_m \tag{6}$$

$$\Delta L_2 = L_{m+2} - L_m = \frac{m+2}{2}\lambda_{m+2} - \frac{m}{2}\lambda_m \tag{7}$$

$$\vdots$$

$$\Delta L_{m'} = L_{m+1} - L_m = \frac{m+m'}{2}\lambda_{m+1} - \frac{m}{2}\lambda_m \tag{8}$$

Accordingly, as is obvious from the formulas (6), (7) and (8), it can be found that the order of interference at the standard m, light wavelength at each minimum point $\lambda_m$, $\lambda_{m+1} \ldots \lambda_{m+m'}$, are required in order to obtain the length variation ($\Delta L$) from the length $L_m$ having been set as the standard to each minimum point.

(Calculation of $\lambda$ and m)

m is calculated from the sample length L which is measured previously. Ideally, m is calculated from the sample length $L_m$ and the wavelength $\lambda_m$ at the point where the order of interference is m by the formula (3)' which is obtained from the above-described formula (3).

$$m = 2L_m/\lambda_m \tag{3)'}$$

In the above case, it is required that the wavelength $\lambda_m$ is obtained from the temperature and pressure at the point where the order of interference is m. Further, it is also required that the sample length at the temperature where the order of interference is m is measured afterward. Thus, the coefficient of linear expansion can be obtained by substituting $L_m$ which is obtained afterward to the controller 60 strictly. However, it is also possible to use a sample length previously measured at room temperature as $L_m$ tentatively.

That is, the measurement starts, and when a first minimum point arises after the measurement starts, the controller 60 calculates the refractive index of the dry air from the temperature and pressure at the point, and calculates the wave length $\lambda_m$. Further, the controller 60 calculates m by the formula (3)', where the sample length measured at a room temperature is regarded as $L_m$.

Even if the calculated value of m includes an error of about 10, the error only has an effect to the measurement result of the length variation $\Delta L$ within a range of 1 [nm]. Thus, it is possible to keep the accuracy of the apparatus sufficiently even when the sample length at a room temperature $L_0$ and the refractive index at the point are regarded as $L_m$ and $\lambda_m$ respectively and the measurement is performed in which the values thereof are input to the controller 60.

As for the light wavelength $\lambda$, the following formula generally has equality where $\lambda v$ represents the wavelength of the light source under vacuum and n represents the refractive index of the dry air which is the medium at the point.

$$\lambda = \frac{\lambda_v}{n} \tag{9}$$

Accordingly, $\lambda_{m+1}, \lambda_{m+2} \ldots \lambda_{m+m'}$ can be calculated by obtaining the refractive index of the gas $n_{m+1}, n_{m+2} \ldots n_{m+m}$ at the points of each minimum point.

Since dry air is used as the gas, the refractive index of the air can be obtained with quite high precision, when "temperature of air" and "pressure of air" are given to the Edlen's empirical formula.

The coefficient of linear expansion measuring apparatus 10 calculates the refractive index of the air at minimum points of the light intensity by measuring the air temperature ($t_{m+1}$, $t_{m+2}$, . . . $t_{m+m'}$) and the air pressure (atmospheric pressure) ($p_{m+1}$, $p_{m+2}$, . . . $p_{m+m'}$) at the individual points where the light intensity is minimum in the measurement.

The controller 60 refers the variation of the light intensity detected by the receiving element, and is capable of recognizing a point where the variation changes from increase to decrease as a maximum point and a point where the variation changes from decrease to increase as a minimum point. Further, the controller 60 can count the order thereof by adding 1 to the numeral value m every time the controller 60 recognizes the maximum point or minimum point.

Further, when a maximum point or minimum point is recognized, the controller 60 calculates the refractive index of dry air $n_{m+1}$, $n_{m+2}$, . . . $n_{m+m'}$ from the temperature detected by the thermocouple 42 and the pressure detected by the barometer 14 at the point.

Accordingly the controller 60 calculates $\Delta L_{m'}$ by the formula (8) every time the light intensity shows a minimum point, and records it to a memory with the detected temperature at each point.

(Length Variation at a Maximum Point)

In the case of constructive interference of light so as to show a maximum point, the case can be thought as same as the case of destructive interference of light by using the relation (2).

$$2L_m = m\lambda_m \rightarrow \quad (10)$$

$$L_m = \frac{m}{2}\lambda_n \quad (10)'$$

$$2L_{m+\frac{1}{2}} = \left(m + \frac{1}{2}\right)\lambda_{m+\frac{1}{2}} \rightarrow \quad (11)$$

$$L_{m+\frac{1}{2}} = \frac{m+\frac{1}{2}}{2}\lambda_{m+\frac{1}{2}} \quad (11)'$$

$$\vdots \qquad \vdots$$

Accordingly, the length variation ($\Delta L$) from the sample length set as a standard $L_m$ to a sample length at each maximum point can be represented as follows.

$$\Delta L_{\frac{1}{2}} = L_{m+\frac{1}{2}} - L_m = \frac{m+\frac{1}{2}}{2}\lambda_{m+\frac{1}{2}} - \frac{m}{2}\lambda_m \quad (12)$$

$$\Delta L_{\frac{3}{2}} = L_{m+\frac{3}{2}} - L_m = \frac{m+\frac{3}{2}}{2}\lambda_{m+\frac{3}{2}} - \frac{m}{2}\lambda_m \quad (13)$$

$$\vdots \qquad \vdots$$

Thus, the length variation from the standard sample length $L_m$ to the sample length at each maximum point can be calculated, where the above formulas (12), (13) . . . is used as same as the case of destructive interference of light. That is, the wavelength at each maximum point is calculated by measuring the refractive index of the air at the point, and finally the length variation $\Delta L$ can be calculated.

The controller 60 calculates $\Delta L_{m'-1/2}$ from the formulas (12) and (13) every time the detected light intensity shows a maximum point, and recodes it to the memory with the detected temperature at the point.

Figure 4:
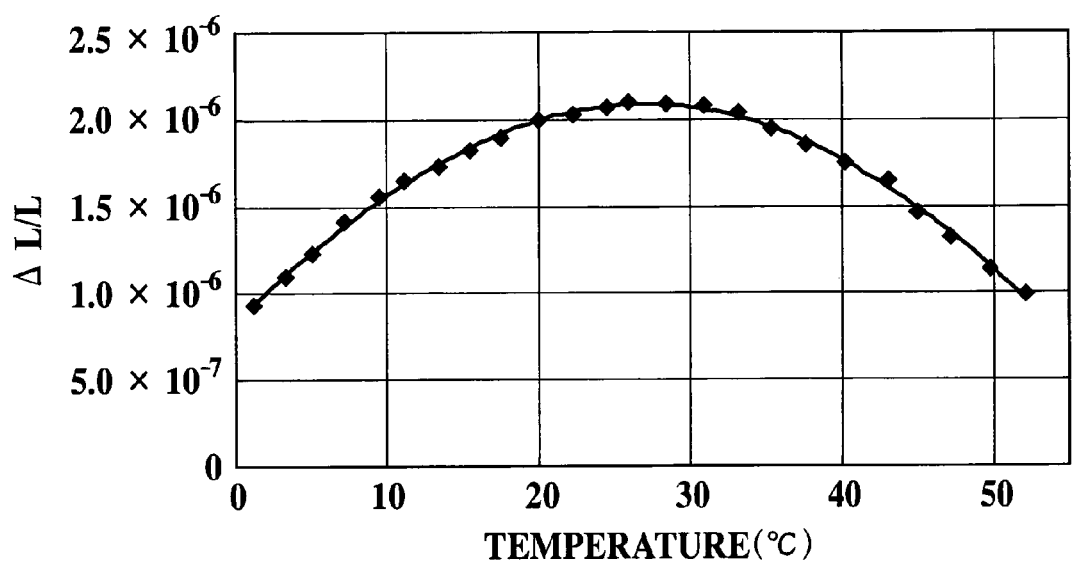
FIG. 4 is a diagram showing the relation between the sample length variation rate (ΔL/L) and the temperature of the sample under each temperature.

The above-mentioned process (3) is described. The controller 60 keeps the data of the length variations of the sample $\Delta L$ at each temperature by the process (2). With reference to the memorized data, let a length of the sample at a certain maximum or minimum point represent L and the length variation at the next minimum or maximum point $\Delta L$ are obtained, and $\Delta L/L$ at each temperature are plotted. Thus the variation as shown in FIG. 4 by way of example can be obtained.

On the other hand, the coefficient of linear expansion of the sample $\alpha$ [1/K] is calculated by the following formula (14), where $\Delta T$ [K] represents the temperature variation in the temperature range where the coefficient of linear expansion is to be obtained.

$$\alpha = (\Delta L/L)/\Delta T \quad (14)$$

Example: A certain case is assumed where the length of the sample L=100 mm, and the temperature variation of 10° C. from 20° C. to 30° C. is given. When the length varies +3 μm, $\Delta T$ becomes +10° C. and $\Delta L$ becomes +3 μm, thus $\alpha$=(+3 μm/100 mm)×(1/+10° C.)=3×10$^{-6}$ [1/° C.] is obtained, where (more properly, the value represents an average coefficient of linear expansion between 20° C. and 30° C.).

When a certain temperature range is set, the controller 60 obtains the temperature variation $\Delta T$ in the range and $\Delta L/L$ at the both ends of the range, so as to calculates $\alpha$.

Figure 5:
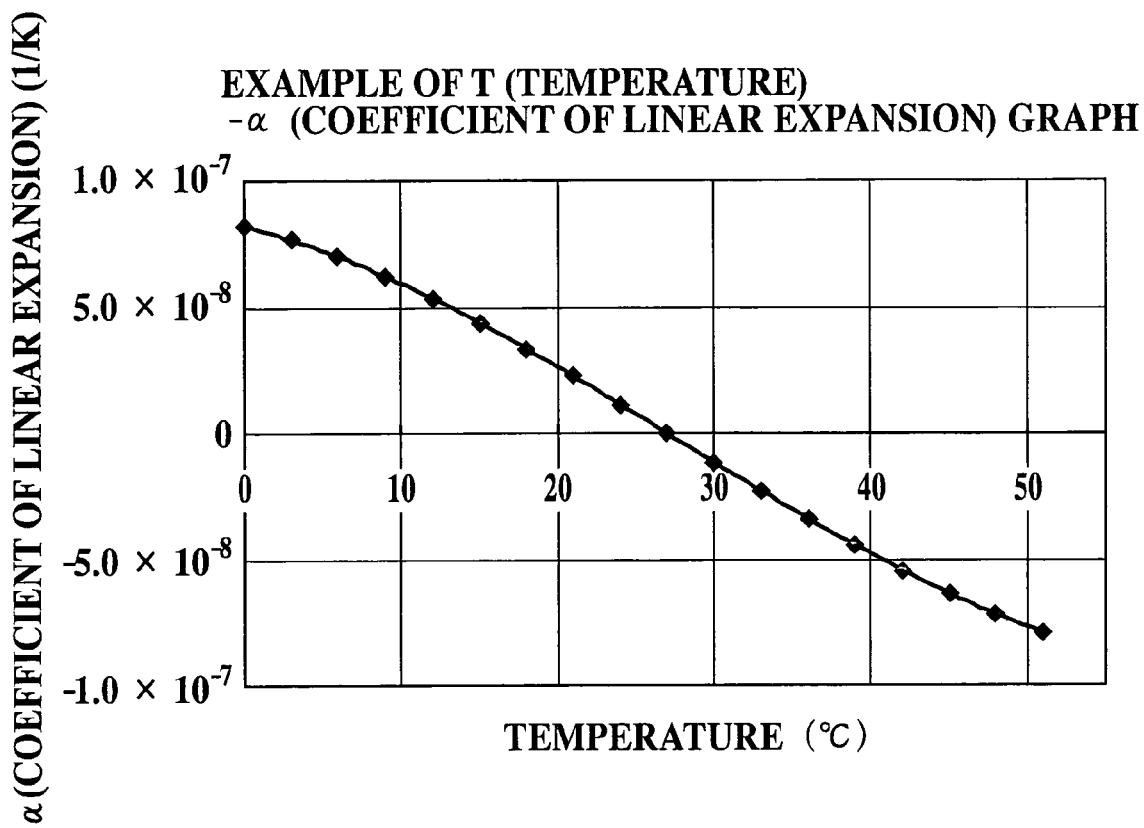
FIG. 5 is a diagram showing the coefficient of linear expansion and the temperature of the sample.

The T-$\alpha$ curve shown in FIG. 5 can be obtained by obtaining the approximation showing plotted $\Delta L/L$ curve, and differentiating it with respect to temperature. The values at each temperature respectively represent the coefficient of linear expansion of the sample at the temperature.

The controller 60 can obtain the length variation of the sample 20 at each temperature so as to obtain the coefficient of linear expansion by performing the above-described processes.

(Measuring Procedure for the Coefficient of Linear Expansion Measuring Apparatus)

First, the user installs the sample 20 and two reflection plates 11 and 12 to the container 30, where the sample 20 is put between them and the reflecting surfaces 11a and 12a are parallel each other.

Further, the internal gas supplying member fills inside of the container 30 with dry air before as well as after the sample 20 and the reflection plates 11 and 12 are installed.

Next, the frequency stabilized laser 71 irradiates the laser light R to the reflecting surfaces 11a and 12a of the reflection plates 11 and 12 placed in the container 30. In this condition where the laser is being irradiated, the temperature regulating member 40 gives a temperature variation to the sample 20 placed in the container 30.

The light receiving element 14 detects the light intensity of the reflected lights reflected on the reflection plates 11 and 12 in the condition where the lights interferes each other, and the controller 60 samples the light intensity variations thereof.

In accordance with the above described processes, the controller 60 calculates the optical path length variation between the reflecting surfaces 11a and 12a of the reflection plates 11 and 12 from the light intensity variation detected by the light receiving element and further corrects a part of the optical path length variation derived from the refractive index variation of the dry air in the container 30 according to the temperature variation, so as to calculate the length variation of the sample 20.

Subsequently, the controller 60 calculates the coefficient of linear expansion of the sample 20 from the calculated length variation of the sample 20 and the temperature variation corresponding to the length variation. A display member may be installed to the controller 60 for displaying the calculated results to the user.

(Effect of the Embodiment)

According to the coefficient of linear expansion measuring apparatus 10 having the above constitution, the light receiving element 14 detects the light intensity variation of the irradiating light having a known wavelength caused by the expansion of the sample 20. Thus, the output of the light receiving element 14 can be converted to signals, so that the controller 60 can calculate the coefficient of linear expansion of the sample 20 with an electrical processes. Therefore, a burden to the user that the user performs the measurement with his visual observation can be reduced compared to earlier development. Further, it becomes possible to perform a measurement having high reproducibility, since the deviation of user's skill has no effect to the measurement compared to the visual observation.

Further the coefficient of linear expansion measuring apparatus 10 dose not require an imaging member for observing interference fringes and an image processing apparatus for processing it, since the apparatus detects an light intensity variation so as to perform the measurement. Thus, it becomes possible to simplify the apparatus and to reduce the cost for the equipment.

The coefficient of linear expansion measuring apparatus 10 performs the measurement in which the sample 20 is placed under dry air atmosphere whose refractive index can be calculated under a predetermined condition. Thus, when the coefficient of linear expansion of the sample 20 having low expansivity is measured in which the light intensity variation to be detected is affected by the expansion variation less than the refractive index variation of the air, the controller 60 can detect the wave pattern of the light intensity in higher frequency compared to the case where a measurement is performed under vacuum within the same temperature range. If the frequency is low, the measurement is subject to the modulation of laser light source and light receiving element. However, the measurement performed by the coefficient of linear expansion measuring apparatus 10 is not affected as described above, and the controller 60 can easily recognize a phase variation even if the measurement is performed in a narrow temperature range. As a result, it becomes possible to reduce an error and to perform a measurement having high reliability.

Since the temperature variation is given to the sample under gas atmosphere, conduction of heat is fast thanks to gas convection. Thus, it becomes possible to perform a rapid measurement since a waiting period for normalize a temperature difference between a sample and optical path is reduced.

Since the temperature variation is given to the sample under gas atmosphere, the points on the continuous wave pattern to be a maximum or minimum point becomes clear. Thus, the error in recognizing a phase variation, which is caused by the modulation of the frequency stabilized laser as a light source and the noise of the light receiving element 14 and the amplifier 15 thereof, can be reduced. As a result, it becomes possible to reduce an error of recognition in the controller 60 and to improve the reliability moreover.

For the same reason described above, the apparatus does not require the equipments having high precision such as a light source in which a modulation hardly occur and a light receiving element in which noise hardly occur. Thus, it becomes possible to simplify the apparatus and to reduce the cost for the apparatus moreover.

The controller 60 obtains length variation of a sample in every interval of peak points recognized clearly in continuous light intensity wave pattern. Further, the refractive index is calculated at every peak points. Thus it becomes possible that the error of the recognition is further prevented and the reliability is further improved.

Since the midair through-hole 21 is provided with the sample 20, an irradiation spot of the irradiating light on the first reflection plate 11 dose not have to be at a corner for being away from the sample 20. Further, since the optical path to be the optical path difference goes inside the sample 20, the temperature difference between the sample and the dry air in the optical path is reduced. Thus, temperature differences in the parts are reduced and it becomes possible to perform a measurement having high reliability and high precision.

In the above-described coefficient of linear expansion measuring apparatus 10, dry air is used as the gas with which inside of the container is filled. However, the gas is not limited thereto, and it is possible to use any gas in which the refractive index thereof can be obtained from a temperature and pressure.

The entire disclosure of Japanese Patent Applications No. 2003-308931 filed on Sep. 1, 2003, including specification, claims, drawings and summary are incorporated herein by reference in its entirety.

What is claimed is:

1. A coefficient of linear expansion measuring apparatus comprising:

two reflection plates between which a sample is put, a container to house the sample and the reflection plates, the container being filled with a gas having known rate of a refractive index variation, a temperature regulating member to set a temperature inside the container variably, a single light source to irradiate an irradiating light having a known wavelength to reflecting surfaces of the reflection plates placed in the container, a light receiving element to receive an reflected lights reflected on the reflection plates in a condition that the reflected lights interferes each other and to detect a light intensity of the reflected lights, and a calculating member to calculate a coefficient of linear expansion of the sample, wherein:

the calculating member calculates an optical path length variation between the reflecting surfaces of the individual reflection plates from an output variation of the light receiving element according to temperature variation in the container, and the calculating member calculates a length variation of the sample by correcting a part of the optical path length variation derived from a refractive index variation of the gas in the container caused by the temperature variation.

2. The coefficient of linear expansion measuring apparatus as claimed in claim 1, wherein when the part of the optical path length variation derived from the refractive index variation of the gas in the container is corrected, the calculating member calculates the length variation of the sample in each interval of peaks which are maximum or minimum in a continuous wave pattern of a light intensity variation output from the light receiving element, and simultaneously refers a refractive index of the gas at temperatures at each of the peaks.

3. The coefficient of linear expansion measuring apparatus as claimed in claim 1, wherein the sample has a midair through-hole to pass the irradiating light having the known wavelength therethrough is provided with the sample.

4. The coefficient of linear expansion measuring apparatus as claimed in claim 2, wherein the sample has a midair through-hole to pass the irradiating light having the known wavelength therethrough is provided with the sample.

5. The coefficient of linear expansion measuring apparatus as claimed in claim 1 further comprising a pressure detecting member to detect a pressure variation of the gas in the container, wherein
the calculating member calculates the refractive index of the gas from a temperature and a detected pressure in the container.

6. The coefficient of linear expansion measuring apparatus as claimed in claim 2 further comprising a pressure detecting member to detect a pressure variation of the gas in the container, wherein
the calculating member calculates the refractive index of the gas from a temperature and a detected pressure in the container.

7. The coefficient of linear expansion measuring apparatus as claimed in claim 3 further comprising a pressure detecting member to detect a pressure variation of the gas in the container, wherein
the calculating member calculates the refractive index of the gas from a temperature and a detected pressure in the container.

8. The coefficient of linear expansion measuring apparatus as claimed in claim 4 further comprising a pressure detecting member to detect a pressure variation of the gas in the container, wherein
the calculating member calculates the refractive index of the gas from a temperature and a detected pressure in the container.

9. A coefficient of linear expansion measuring method comprising:
housing two reflection plates and a sample to a container being capable of controlling a temperature, where a sample is put between the reflection plates and reflecting surfaces of reflection plates are parallel with each other,
filling the container with a gas having a known refractive index variation before as well as after the housing,
irradiating an irradiating light having a known wavelength to the reflecting surfaces of the reflection plates placed in the container by a single light source,
detecting a light intensity of reflected lights reflected on the reflection plates in a condition that the reflected lights interfere each other, while a temperature variation is given to the sample placed in the container,
calculating an optical path length variation between the reflecting surfaces of the reflection plates from an output variation of the Light receiving element according to the temperature variation,
correcting a part of the optical path length variation derived from a refractive index variation of the gas in the container caused by the temperature variation, and calculating a length variation of the sample.

10. The coefficient of linear expansion measuring method as claimed in claim 9, wherein when the part of the optical path length variation derived from the refractive index variation of the gas in the container is corrected, the length variation of the sample is calculated in each interval of peaks which are maximum or minimum in a continuous wave pattern of a light intensity variation output from the light receiving element, and simultaneously a refractive index of the gas at temperatures at the individual peaks is referred.

11. The coefficient of linear expansion measuring method as claimed in claim 9, wherein a midair through-hole is provided with the sample and
a measurement is performed in which the irradiating light having the known wavelength transmits one reflection plate, passes through the midair through-hole and is irradiated to other reflection plate.

12. The coefficient of linear expansion measuring method as claimed in claim 10, wherein a midair through-hole is provided with the sample and
a measurement is performed in which the irradiating light having the known wavelength transmits one reflection plate, passes through the midair through-hole and is irradiated to other reflection plate.

13. The coefficient of linear expansion measuring method as claimed in claim 9, further comprising:
detecting a pressure variation of the gas in the container, and
calculating the refractive index of the gas from a temperature and a detected pressure in the container.

14. The coefficient of linear expansion measuring method as claimed in claim 10, further comprising:
detecting a pressure variation of the gas in the container, and
calculating the refractive index of the gas from a temperature and a detected pressure in the container.

15. The coefficient of linear expansion measuring method as claimed in claim 11, further comprising:
detecting a pressure variation of the gas in the container, and
calculating the refractive index of the gas from a temperature and a detected pressure in the container.

16. The coefficient of linear expansion measuring method as claimed in claim 12, further comprising:
detecting a pressure variation of the gas in the container, and
calculating the refractive index of the gas from a temperature and a detected pressure in the container.

17. The coefficient of linear expansion measuring apparatus as claimed in claim 1, wherein the gas is dry air.

18. The coefficient of linear expansion measuring apparatus as claimed in claim 8, wherein the gas is dry air.

19. The coefficient of linear expansion measuring method as claimed in claim 9, wherein the gas is dry air.

20. The coefficient of linear expansion measuring method as claimed in claim 16, wherein the gas is dry air.

* * * * *

UNITED STATES PATENT AND TRADEMARK OFFICE
CERTIFICATE OF CORRECTION

PATENT NO. : 7,164,481 B2
APPLICATION NO. : 10/927057
DATED : January 16, 2007
INVENTOR(S) : Nobuo Kawasaki et al.

It is certified that error appears in the above-identified patent and that said Letters Patent is hereby corrected as shown below:

Column 1, Line 48:

Delete: "Summery"
Replace with: --Summary--

Column 2, Line 33:

Delete "temperature, However,"
Replace with: --temperature. However,--

Column 3, Line 50:

Delete: "dose"
Replace with: --does--

Column 5, Line 41:

Delete: "dose"
Replace with: --does--

Column 7, Line 26:

Delete: "dose"
Replace with: --does--

Column 12, Line 52:

Delete: ")" after "Pvapor"

Column 13, Line 41:

Delete: "representas"
Replace with: --represent as--

Column 14, Line 8:

Delete:
$$\text{``}\Delta L_{m'} = L_{m+1} - L_m \frac{m+m'}{2} = \lambda_{m+1} \frac{m}{2} - \lambda_m \quad (8)\text{''}$$

Replace with:
$$--\Delta L_{m'} = L_{m+m'} - L_m = \frac{m+m'}{2}\lambda_{m+m'} - \frac{m}{2}\lambda_m \quad ..(8)--$$

Column 18, Line 17:

Delete: "dose"
Replace with: --does--

UNITED STATES PATENT AND TRADEMARK OFFICE
CERTIFICATE OF CORRECTION

PATENT NO. : 7,164,481 B2
APPLICATION NO. : 10/927057
DATED : January 16, 2007
INVENTOR(S) : Nobuo Kawasaki et al.

It is certified that error appears in the above-identified patent and that said Letters Patent is hereby corrected as shown below:

Column 11, Line 62:

Delete: "dose"
Replace with: "does"

Column 19, Line 60:

Delete: "Light"
Replace with: "light"

Signed and Sealed this

Thirty-first Day of July, 2007

JON W. DUDAS
*Director of the United States Patent and Trademark Office*